US 6,525,534 B2

(12) United States Patent
Akkurt et al.

(10) Patent No.: US 6,525,534 B2
(45) Date of Patent: Feb. 25, 2003

(54) SYSTEM AND METHODS FOR NMR SIGNAL PROCESSING WITHOUT PHASE ALTERNATED PAIR STACKING

(75) Inventors: Ridvan Akkurt, Kingwood, TX (US); Ronald E. Cherry, Kingwood, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 0 days.

(21) Appl. No.: 09/882,316

(22) Filed: Jun. 15, 2001

(65) Prior Publication Data

US 2002/0196017 A1 Dec. 26, 2002

(51) Int. Cl.⁷ .................................................. G01V 3/00
(52) U.S. Cl. ........................................ 324/303; 324/300
(58) Field of Search ................................ 324/303, 300, 324/307, 309, 318, 338

(56) References Cited

U.S. PATENT DOCUMENTS

| | | | |
|---|---|---|---|
| 3,213,357 A | 10/1965 | Brown et al. ............... | 224/303 |
| 4,686,364 A | 8/1987 | Herron ........................ | 250/256 |
| 4,707,658 A | 11/1987 | Frahm et al. ............... | 324/309 |
| 4,710,713 A | 12/1987 | Taicher et al. .............. | 324/303 |
| 4,717,876 A | 1/1988 | Masi et al. .................. | 324/303 |
| 4,717,877 A | 1/1988 | Taicher et al. .............. | 324/303 |

(List continued on next page.)

FOREIGN PATENT DOCUMENTS

| | | | | |
|---|---|---|---|---|
| EP | 0 295 134 A2 | 12/1988 | ............ | G01V/3/32 |
| EP | 0 581 666 A3 | 2/1994 | ............ | G01V/3/32 |
| EP | 0 649 035 B1 | 4/1995 | ............ | G01V/3/32 |
| GB | 2 056 082 A | 7/1980 | .......... | G01N/24/08 |
| WO | WO 92/10768 | 6/1992 | ............ | G01V/3/32 |
| WO | WO 98/25164 | 6/1998 | ............ | G01V/3/32 |

(List continued on next page.)

OTHER PUBLICATIONS

Akkurt et al., "Selection of Optimal Acquisition Parameters for MRIL Logs," SPWLA 37th Annual Logging Symposium, Jun. 16–19, 1996.
Akkurt et al., "NMR Logging of Natural Gas Reservoirs," SPWLA 36th Annual Logging Symosium (Jun. 26–29, 1995).

(List continued on next page.)

Primary Examiner—Edward Lefkowitz
Assistant Examiner—Brij B. Shrivastav
(74) Attorney, Agent, or Firm—Pennie & Edmonds LLP

(57) ABSTRACT

A system and methods for improving the vertical resolution of NMR logs based on data acquisition methods and signal processing techniques that need not apply Phase Alternated Pair Stacking (PAPS). The method is based on reducing the level of coherent non-formation signals, by estimating these signals and removing the estimates from the underlying NMR pulse echo trains. Once the estimated non-formation signal components have been removed, standard NMR processing methods are applied to derive petrophysical properties of the formation being investigated. In a preferred embodiment the NOPAPS method of this invention is practiced along with a data acquisition sequence, which can be used to further increase the logging speed of the tool or vertical resolution of the measurements.

25 Claims, 7 Drawing Sheets

U.S. PATENT DOCUMENTS

| | | | |
|---|---|---|---|
| 4,717,878 A | 1/1988 | Taicher et al. | 324/303 |
| 4,728,892 A | 3/1988 | Vinegar et al. | 324/309 |
| 4,933,638 A | 6/1990 | Kenyon et al. | 324/303 |
| 5,023,551 A | 6/1991 | Kleinberg et al. | 324/303 |
| 5,055,787 A | 10/1991 | Kleinberg et al. | 324/303 |
| 5,055,788 A | 10/1991 | Kleinberg et al. | 324/303 |
| 5,212,447 A | 5/1993 | Paltiel | 324/300 |
| 5,280,243 A | 1/1994 | Miller | 324/303 |
| 5,291,137 A | 3/1994 | Freedman | 324/303 |
| 5,309,098 A | 5/1994 | Coates et al. | 324/303 |
| 5,363,041 A | 11/1994 | Sezginer | 324/303 |
| 5,365,171 A | 11/1994 | Buess et al. | 324/307 |
| 5,381,092 A | 1/1995 | Freedman | 324/303 |
| 5,387,865 A | 2/1995 | Jerosch-Herold et al. | 324/303 |
| 5,412,320 A | 5/1995 | Coates | 324/303 |
| 5,486,762 A | 1/1996 | Freedman et al. | 324/303 |
| 5,497,087 A | 3/1996 | Vinegar et al. | 324/303 |
| 5,498,960 A | 3/1996 | Vinegar et al. | 324/303 |
| 5,517,115 A | 5/1996 | Prammer | 324/303 |
| 5,557,200 A | 9/1996 | Coates | 324/303 |
| 5,557,201 A | 9/1996 | Kleinberg et al. | 324/303 |
| 5,629,623 A | 5/1997 | Sezginer et al. | 324/303 |
| 5,680,043 A | 10/1997 | Hurlimann et al. | 324/303 |
| 5,696,448 A | 12/1997 | Coates et al. | 324/303 |
| 5,705,927 A | 1/1998 | Sezginer et al. | 324/303 |
| 5,757,186 A | 5/1998 | Taicher et al. | 324/303 |
| 5,796,252 A | 8/1998 | Kleinberg et al. | 324/303 |
| 5,936,405 A | 8/1999 | Prammer et al. | 324/303 |
| 5,977,768 A | 11/1999 | Sezginer et al. | 324/303 |
| 6,005,389 A | 12/1999 | Prammer | 324/303 |
| 6,023,163 A | 2/2000 | Flaum et al. | 324/303 |
| 6,049,205 A | 4/2000 | Taicher et al. | 324/303 |
| 6,051,973 A | 4/2000 | Prammer | 324/303 |
| 6,107,796 A | 8/2000 | Prammer | 324/303 |
| 6,107,797 A | 8/2000 | Sezginer | 324/303 |
| 6,111,408 A | 8/2000 | Blades et al. | 324/303 |
| 6,121,774 A | 9/2000 | Sun et al. | 324/303 |
| 6,133,735 A | 10/2000 | Hurllmann et al. | 324/303 |
| 6,140,817 A | 10/2000 | Flaum et al. | 324/303 |
| 6,229,308 B1 | 5/2001 | Freedman | 324/303 |
| 6,242,912 B1 * | 6/2001 | Prammer et al. | 324/303 |
| 6,255,819 B1 * | 7/2001 | Day et al. | 324/303 |
| 6,337,568 B1 * | 1/2002 | Tutunji et al. | 234/303 |

OTHER PUBLICATIONS

Brown et al., "Nuclear Magnetism Logging," Transactions of the American Institute of Mining, Metallurgical, and Petroleum Engineers, vol. 219 (1960), pp. 199–207.

Chandler et al., "Improved Log Quality with a Dual–Frequency Pulsed NMR Tool," Society of Petroleum Engineers (1994) pp. 23–35.

Chandler et al., "Reliable Nuclear Magnetism Logging—With Examples in Effective Porosity and Residual Oil Saturation," SPWLA—28th Annual Logging Symposium, vol. 1, Manuscript C, (1987).

Chen et al., "Improving the Accuracy of NMR Relaxation Distribution Analysis in Clay–Rich Reservoirs and Core Samples," paper SCA 9702, in 1997 international symposium proceedings: Society of Professional Well Log Analysts, Society of Core Analysts Chapter–at large, p. 10, 1997.

Chen et al., "Estimation of Hydrocarbon Viscosity with Multiple TE Dual Wait–Time MRIL Logs," Society of Petroleum Engineers, SPE 49009, 1998.

Dunn et al., "A Method for Inverting NMR Data Sets With Different Signal to Noise Ratios," SPWLA 39th Annual Logging Symposium, May 26–29, 1998.

Edwards et al., "Improved NMR Well Logs From Time–Dependent Echo Filtering," SPWLA 37th Annual Logging Symposium, Jun. 16–19, 1996.

Edwards et al., "Effects of Tool Design and Logging Speed on $T_2$ NMR Log Data," SPWLA 38th Annual Logging Symposium, Jun. 15–18, 1997.

Jackson et al., "Western Gas Sands Project Los Alamos NMR Well Logging Tool Development," Los Alamos National Laboratory (Oct. 1981—Sep. 1982) pp. 1–28.

Jackson et al., "Nuclear Magnetic Resonance Well Logging," The Log Analyst, Sep.–Oct., 1984, pp. 16–30.

Kenyon et al., "Pore–Size Distribution and NMR in Microporous Cherty Sandstones," SPWLA Thirtieth Annual Logging Symposium (Jun. 11–14, 1989), pp. 1–24.

Kleinberg et al., "Novel NMR Apparatus for Investigating an External Sample," *Journal of Magnetic Resonance*, (1992) pp. 466–485.

Kleinberg et al., "Nuclear Magnetic Resonance of Rocks: $T_1$ vs. $T_2$," Society of Petroleum Engineers, SPE 26470, 1993, pp. 553–563.

Kleinberg et al., "NMR Properties of Reservoir Fluids," The Log Analyst, Nov.–Dec. 1996, pp. 20–32.

Menger et al., "A New Algorithm for Analysis of NMR Logging Data," Society of Petroleum Engineers, Inc., SPE 49013, 1998.

Miller et al., "Spin Echo Magnetic Resonance Logging: Porosity and Free Fluid Index Determination," *Society of Petroleum Engineers*, SPE 20561 (1990), pp. 321–334.

Morriss et al., "Field Test of an Experimental Pulsed Nuclear Magnetism Tool," SPWLA Annual Logging Symposium (Jun. 13–16, 1993), pp. 1–23.

Prammer et al., "Theory and Operation of a New, Multi–Volume, NMR Logging System," SPWLA 40th Annual Logging Symposium, May 30–Jun. 3, 1999.

Prammer et al., "A New Multiband Generation of NMR Logging Tools," Society of Petroleum Engineers, SPE 49011, 1998.

Prammer et al., "Measurements of Clay–Bound Water and Total Porosity by Magnetic Resonance Logging," Society of Petroleum Engineers, SPE 36522, 1996.

Prammer, M.G., "NMR Pore Size Distributions and Permeability at the Well Site," *Society of Petroleum Engineers*, SPE 28368, (1994) pp. 55–64.

*Schlumberger Technology News—Oilfield Bulletin*, "Fifth Generation Nuclear Magnetic Resonance Logging Tool: A Major Advance in Producibility Measurement Technology," (Jul. 1995) (2 pp.).

*Schlumberger Wireline & Testing*, "Combinable Magnetic Resonance tool reliably indicates water–free production and reveals hard–to–find pay zones," (Jun. 1995).

Singer et al., "Fast NMR Logging for Bound Fluid and Permeability," SPWLA 38th Annual Logging Symposium, Jun. 15–18, 1997.

* cited by examiner

SYSTEM AND METHODS FOR NMR SIGNAL PROCESSING WITHOUT PHASE ALTERNATED PAIR STACKING

FIELD OF THE INVENTION

The present invention concerns nuclear magnetic resonance (NMR) logging and more specifically relates to a system and methods for NMR data acquisition and processing, which improve the vertical resolution and/or logging speed at which NMR logs can be acquired using NMR logging tools.

BACKGROUND OF THE INVENTION

In oil and gas exploration it is desirable to understand the structure and properties of the geological formation surrounding a borehole, in order to determine if the formation contains hydrocarbon resources (oil and/or gas), to estimate the amount and producibility of hydrocarbon contained in the formation, and to evaluate the best options for completing the well in production. A significant aid in this evaluation is the use of wireline logging and/or logging-while-drilling (LWD) measurements of the formation surrounding the borehole (referred to collectively as "logs" or "log measurements"). Typically, one or more logging tools are lowered into the borehole and the tool readings or measurement logs are recorded as the tools traverse the borehole. These measurement logs are used to infer the desired formation properties.

In recent years nuclear magnetic resonance (NMR) logging has become very important for purposes of formation evaluation and is one of the preferred methods for determining formation parameters. Improvements in the NMR logging tools, as well as advances in data analysis and interpretation allow log analysts to generate detailed reservoir description reports, including clay-bound and capillary-bound related porosity, estimates of the amounts of bound and free fluids, fluid types (i.e., oil, gas and water), permeability and other properties of interest.

NMR tools used in practical applications include, for example, the centralized MRIL® tool made by NUMAR Corporation, a Halliburton company, and the sidewall CMR tool made by Schlumberger. The MRIL® tool is described, for example, in U.S. Pat. No. 4,710,713 to Taicher et al. and in various other publications including: "Spin Echo Magnetic Resonance Logging: Porosity and Free Fluid Index Determination," by Miller, Paltiel, Gillen, Granot and Bouton, SPE 20561, 65th Annual Technical Conference of the SPE, New Orleans, La., Sep. 23–26, 1990; "Improved Log Quality With a Dual-Frequency Pulsed NMR Tool," by Chandler, Drack, Miller and Prammer, SPE 28365, 69th Annual Technical Conference of the SPE, New Orleans, La., Sep. 25–28, 1994. Certain details of the structure and the use of the MRIL® tool, as well as the interpretation of various measurement parameters are also discussed in U.S. Pat. Nos. 4,717,876; 4,717,877; 4,717,878; 5,212,447; 5,280,243; 5,309,098; 5,412,320; 5,517,115; 5,557,200; 5,696,448; 5,936,405; 6,005,389; 6,03,164; 6,051,973; 6,107,796 and 6,111,408. The structure and operation of the Schlumberger CMR tool is described, for example, in U.S. Pat. Nos. 4,939,648; 5,055,787 and 5,055,788 and further in "Novel NMR Apparatus for Investigating an External Sample," by Kleinberg, Sezginer and Griffin, J. Magn. Reson. 97, 466–485, 1992; and "An Improved NMR Tool Design for Faster Logging," D. McKeon et al., SPWLA 40$^{th}$ Annual Logging Symposium, May–June 1999. The content of the above patents is hereby expressly incorporated by reference for all purposes, and all non-patent references are incorporated by reference for background.

NMR $T_2$ logging is different from most other logging methods in that the measurement is not instantaneous. Each measurement cycle, including the wait time needed for polarization, can take several seconds. Furthermore, as discussed below, several cycles usually have to be stacked to achieve adequate signal-to-noise ratio (SNR).

If a cycle takes T seconds to complete, and N cycles must be stacked, the vertical resolution of a measurement is proportional to vNT, where v is the logging speed. Clearly, the longer the cycle times and faster the logging speeds, the worse the vertical resolution. Therefore, an ever-present challenge in NMR logging is to design tools that can log faster, while retaining acceptable vertical resolution. Overcoming this challenge is an extremely important task. Several innovations towards faster logging have been put into practice over the past several years.

One such innovation was the introduction of multi-frequency logging in the early 1990s. (With reference to the listing in the back of this section, see, for example, Chandler et al, 1994). The benefit of multi-frequency logging is that the tools acquire data simultaneously over several frequencies, and the additional SNR available can be used to speed up logging as well as to obtain higher quality results. The state-of-the-art in multi-frequency logging is the MRIL®-Prime tool by Numar Corporation, which currently can operate on 9 frequencies.

Another innovation was the introduction of simultaneous acquisition of partially and fully polarized echo trains with different SNR. (See, for example, Prammer et al, 1996). Proper total porosity measurements require: (1) a short interecho time $T_e$ to sample fast decays, (2) high SNR to reduce the uncertainty in the estimation of fast decays, (3) long sampling time ($N_e T_e$ where $N_e$ is the number of echoes) for adequate sampling of longer decays. It is practically impossible to achieve all these objectives with a unique wait time $T_w$, $T_e$ and $N_e$ combination; while maintaining acceptable logging speeds and vertical resolution. Therefore, a good solution is to optimize the acquisition by mixing partially and fully recovered data with different measurement parameters $T_w$, $T_e$, $N_e$ and desired SNR. Another closely related innovation was the concept of simultaneous-inversion, where data acquired with different measurement parameters is inverted simultaneously using forward models that properly account for the differences in fluid NMR properties, acquisition parameters and noise levels. (See, Looyestijn, 1996, and Dunn, et al. 1998).

Yet another innovation was the use of pre-polarization (See, for example, Akkurt, 1990). In this approach the cycle time for each measurement is shortened, by placing static magnets above the antenna section to realize additional polarization during tool motion. Current generation NMR tools generally contain pre-polarization sections, allowing overall faster logging.

However, in the search for faster NMR logging a problem still exists because of the need to remove coherent non-formation signals. Such removal has been done traditionally using Phase Alternated Pair Stacking (PAPS). PAPS is the most widely used method in NMR logging to remove coherent non-formation signals, typically referred to as bias (or ringing). Since bias is a frequency dependent phenomenon, the two CPMGs making up a phase alternated pair must be acquired at the same frequency. This requirement places an undesirable upper limit to the vertical resolution of NMR logs. The rationale for the use of PAPS in the prior art is described below.

An actual NMR measurement involves a plurality of pulses grouped into pulse sequences, most frequently of the type known in the art as Carr-Purcell-Meiboom-Gill (CMPG) pulsed spin echo sequences. As known in the art, each CPMG sequence consists of a 90-degree (i.e., π/2) pulse followed by a large number of 180-degree (i.e., π) pulses. The 90-degree pulse rotates the proton spins into the transverse plane and the 180-degree pulses generate a sequence of spin echoes by refocusing the transverse magnetization after each spin echo.

It should be apparent that it is important for the NMR measurements to register only signals that are generated by the formation of interest. However, non-formation signals— often referred to as "offset" or "ringing" signals—arise for a variety of reasons. For example, they may be caused by the high-sensitivity tool electronics (e.g., instrumentation biases and offsets), or may be due to magnetostrictive effects (e.g., "ringing") that arise from interactions between pulsed magnetic fields and electronic or magnetic components in the tool. For example, when RF pulses are applied to the antenna, the magnet can become physically deformed by magnetostriction. After each RF pulse is turned off, the magnet tends to return to its original shape in a series of damped mechanical oscillations, known as "ringing." Ringing induces voltages in the antenna, which can interfere with measurement of the voltages induced by the spin echoes.

A method known in the art for reducing the effect of offsets, ringing and possibly other non-formation signals is to make spin echo measurements in predetermined cycles. Typically, two pulse sequences of opposite phase are acquired to cancel electronic offsets and 180-degree ringing. The pair of pulse sequences is called a phase-alternated pair (PAP). PAP measurements are performed by making a second set of spin echo measurements starting with an original transverse alignment (90 degree) RF pulse, which is inverted in phase from the 90 degree pulse used to start the first set of spin echo measurements. Voltages induced in the antenna during the second set of spin echo measurements are inverted in polarity from the voltages induced in the first set of measurements. The signals from the second set of measurements can then be subtracted from the signals in the first set of measurements to substantially remove coherent noise, such as the ringing-induced signals. (For simplicity, in the following discussion "bias" will be used as a catch-all term designating undesirable non-formation signals). Accordingly, in the "PAP method" successive echo-train signals are acquired from the formation that are alternately in-phase and anti-phase with respect to signals that are generated outside the formation; thus, a typical PAP simply comprises any adjacent pair of in-phase and anti-phase CPMG echo-trains. An implicit assumption in this operation is that the tool-related, non-formation signals in an echo-train can somehow be characterized, and that they change little, or even not at all, between successive echo-trains.

Mathematically, the PAP method can be illustrated as follows. Suppose that an individual spin echo train ($CPMG_0$) can be characterized as a summation of a decaying NMR signal from the formation ($S_0$), a non-formation signal ($O_0$), and random or thermal noise ($n_0$), so that $CPMG_0 = S_0 + O_0 + n_0$. The subsequent phase-alternated echo-train ($CPMG_1$), is then given by $CPMG_1 = -S_1 + O_1 + n_1$. Since changes in the non-formation signal are assumed to be minimal, the difference between the two echo-trains (PAP) cancels the non-formation signals, leaving an echo-rain that is a composite of the signals and the noise, i.e.:

$$PAP = (S_0 + S_1) + n_\Delta.$$

Accordingly, in the prior art non-formation noise is removed using the above PAP process, in which one or more phase alternated pair signals are subtracted to remove the bias. The two acquisition sequences in each phase alternate pairs must be separated in time by $T_w$, the time to repolarize the media. During logging, the tool is moving at a speed v, so that the PAPs are separated by a distance equal to $v*T_w$. Clearly, this limits the vertical resolution achievable with the tool. Additionally, for NMR logging tools operating at N frequencies, the numbers of PAPs stacked must be a multiple of N. Since each PAP comprises two echo-trains, the minimum stacking for the MRIL tool is two times the number of acquired frequencies. There are two problems associated with this approach. First, in formations with high signal-levels, the approach results in more stacking than is necessary to provide adequate signal-to-noise ratio. On the other hand, for those formations with lower signal-levels, in which more stacking is required to obtain adequate SNR, it is necessary to select an amount of stacking, which is a multiple of the minimum stacking. This is undesirable at least because the extra averaging introduces undesirable processing delays and reduces the maximum vertical resolution.

Focusing next on another deficiency associated with the prior art, as a consequence of the PAP method, the "best-possible" effective vertical resolution of an NMR log acquired with a moving tool is a combination of both the inherent vertical resolution of the tool antenna—the antenna aperture—and the distance traveled between the pair of echo-train measurements that comprise a PAP. As discussed above, however, in many logging situations the vertical resolution is further compromised by the need to average data from multiple PAPs to ensure an adequate signal-to-noise ratio (SNR) for confident data analysis. For example, it is known in the art to improve the SNR of NMR well logging measurements by averaging a plurality of PAPs, typically eight or more. It will be apparent that the vertical resolution of the tool is reduced correspondingly.

Enhancing the resolution of the logs is a significant problem, because subsurface formations are generally heterogeneous, so that porosity, saturation and lithology vary with position. A common example of heterogeneity is the presence in the formation of geological layers, or beds. Because logging tools have a nonzero volume of investigation, more than one layer may lie within the volume of investigation of a tool. In such cases, the petrophysical evaluation of one layer may be distorted by the presence of another layer falling within the larger volume of investigation of the tool. The above phenomenon leads to a specific problem in the analysis of subsurface formations that include one or more underground layers, especially when the layers are thin compared with the vertical resolution of the measuring tool. Such layers have become subject to significant commercial interest because of their production potential. Any knowledge about the composition and properties of such layered formations that helps better estimate their production potential has thus become increasingly valuable.

To address some of the issues it helps to have a mathematical description of the underlying physical phenomena. In general, the complex NMR CPMG signal y(t) has three components: (1) the formation signal s(t), (2) the bias B, (3) the random noise components $n_x(t)$ and $n_y(t)$, as shown in the following expression:

$$y(t) = s(t)e^{j\theta_s} + Be^{j\theta_b} + n_x(t) + jn_y(t) \qquad (1)$$

where $j = \sqrt{-1}$. In the above equation, $n_x(t)$ and $n_y(t)$ are zero-mean Gaussian and uncorrelated. It should be noted that the formation signal angle $\theta_s$ and bias angle $\theta_b$, as well as the bias B are treated as time-independent parameters. Also, the NMR signal is actually a discrete function sampled at interecho time $T_e$, even though it is treated as a continuous function of time here for ease of notation.

Assuming that the random noise components in Eq. (1) can be minimized by signal averaging (stacking), extracting the formation signal requires the elimination of the bias. As noted above, the method currently used is to employ PAPS. The PAPS process uses the phase sensitivity of the formation signal to the phase of the RF pulses. In general, in the second CPMG sequence of a phase alternated pair, the phase of the 90° pulse is varied by 180°. Alternatively, one can invert the phase of the 180° pulses, instead of the 90° pulse in the phase alternated pair. Using this alternative method, given two CPMGs $y_+(t)$ and $y_-(t)$ one can obtain:

$$y_+(t) = s(t)e^{j\theta_s} + Be^{j\theta_b}$$

$$y_-(t) = s(t)e^{j\theta_s} - Be^{j\theta_b}$$

where the phase of the 180° pulses in $y_-(t)$ differs by 180° from the phase of the $y_+(t)$ sequence. Clearly, the formation signal can be obtained from the sum of the CPMGs:

$$s(t)e^{j\theta_s} = \frac{y_+(t) + y_-(t)}{2} \qquad (2)$$

The final step in the extraction of the formation signal involves multiplication by the phasor $e^{-j\theta_s}$, followed by taking the real part of the complex signal. Note that the random noise components have been neglected from the above discussion for sake of simplicity.

Bias is a frequency (and interecho spacing $T_e$) dependent phenomenon. Therefore, phase alternated pairs acquired at different frequencies can not be stacked arbitrarily: the stacking must be confined to a certain frequency. This requirement also defines the vertical resolution of logs processed using PAPS. The height of the formation volume associated with a phase-alternated-pair (PAP) is proportional to the logging speed:

$$H_{PAP} = v[T_w + 2(N_e T_e)] + L \qquad (3)$$

where $H_{PAP}$ is the formation volume height, v is the logging speed, $T_w$ is the wait time, $N_e$ is the number of echoes, $T_e$ is the interecho time, and L is the antenna length. Faster logging speeds and larger antennas result in the further degradation of vertical resolution. Note that $H_{PAP}$ above is not a definition for the vertical resolution of an NMR log, it simply represents the height of the formation volume, which is related to vertical resolution.

Faster logging speeds and a larger antenna result in the further degradation of vertical resolution. Also note that in the case of multi-frequency logging, where several phase-alternated-pairs are stacked, the above definition of $H_{PAP}$ corresponds to the lower limit of the height of the formation volume. If $H_{st}$ is the height associated with the stack of several phase-alternated-pairs, then generally $$H_{st} \gg H.$$

The constraints imposed by the use of PAPS have been recognized in the prior art, and some methods have been proposed in the past to address the resulting issues. An example for such a process is the Single Echo Train Offset Removal (SETOR) method, described in co-pending application Ser. No.09/736,754 filed Dec. 14, 2000, to the assignee of the present application, which is hereby incorporated by reference. In the SETOR method non-formation signals are characterized and removed from the underlying NMR spin echo signals in separate steps. In particular, to analyze the bias signals first two or more acquisition sequences are combined in such a matter as to obtain an estimate of the ringing component of the signal, which is assumed to be a constant or a slowly varying function. In the following step of the process, various signal processing or statistical methods are applied to remove the estimated ringing component from the acquisition sequences. (See also, Sigal et al, 2000). The bias signal is estimated by combining phase-alternated pairs. In particular, the method relies on taking the difference between the $y_+(t)$ and $y_-(t)$ signals in Eq. (2) to estimate B:

One problem with this approach is that it still relies on the use of phase alternated pairs. Further, it will be appreciated that in the above expression one has to rely on the corresponding formation signals canceling out, which condition may not hold in all practical cases.

Another prior art method is disclosed in U.S. Pat. No. 6,121,774, which is also incorporated by reference for all purposes. In this patent an oscillating magnetic field is applied to the volume of formation according to a selected pulse sequence for a plurality of cycles, so that a NMR signal is generated in the volume of formation. During a first time period of a single pulse sequence cycle, a first plurality of oscillating pulses are applied to the volume of formation and signals generated in the formation are measured. The measured signals comprise a ringing component and a plurality of spin-echoes. Next, the spin-echoes are eliminated so that during a second time period of the single pulse sequence cycle the measured signals comprise the ringing component and substantially exclude the spin-echoes. Finally, signals measured during the first time period are corrected to eliminate the ringing component. Thus, according to the patented approach during the second time period the spin-echoes and stimulated echoes may be eliminated by repeatedly applying a short pulse followed by a time delay in order to spoil the stimulated echoes and the spin-echoes. Alternatively, during the second time period, a phase alternated pulse sequence may be applied to spoil the stimulated echoes and the spin-echoes.

While the patented method addresses some of the problems associated with the prior art, it also has deficiencies. For example, the proposed method works only if the data is acquired with the pulse sequences used in the method. Therefore, old logs can not be processed with this method. Further, the method requires special pulses be programmed into the CPMG or other routinely used sequences, thus requiring special coding work. Similarly, dissemination of the echo train into various time intervals is required, which complicates the method. Further, in this method the formation signal has to be killed at some point to "reveal" the ringing and other components. Assuming that T is the time during which the formation signal is allowed to come in, and Tt the total duration of the pulse sequence (Tt>T). If T is too short (T<$2T_{2max}$), the resolution of the $T_2$ spectrum will suffer. Long decay components will shift to faster times, biasing the $T_2$ spectrum. Another potential problem is that the method of the U.S. Pat. No. 6,121,774 patent requires killer-pulses to "kills" the signal. It will be appreciated that for various reasons the killer pulses may not work effectively, or not at all. These and other deficiencies associated with the prior art are addressed in accordance with the present invention using a novel method, which does not need any PAPS.

The interested reader is directed for additional background information to the disclosure of the following publications.

REFERENCES

Akkurt, R., 1990, Effect of Motion in NMR Logging, Ph.D. Thesis, Colorado School of Mines, Golden, Colo.

Chandler, R. N., Drack, E. O., Miller, M. N., and Prammer, M. G., 1994, Improved Log Quality with a Dual-Frequency Pulsed NMR Tool, SPE-28365, presented at the 1994 SPE Annual Technical Conference and Exhibition held in New Orleans, La.

Dunn, K-J, Bergman, D. J., LaTorraca, G. A., Stonard, S. M., and Crowe, M. B., 1998, A Method for Inverting NMR Data Sets with Different Signal to Noise Ratios, paper JJ, presented at the 39$^{th}$ Annual Logging Symposium, SPWLA, Keystone, Colo.

Fukushima, E., and Roeder, S. B. W., 1979, Spurious Ringing in Pulse NMR, Journal of Magnetic Resonance, Vol. 33, p. 199.

Looyestijn, W. J., 1996, Determination of Oil Saturation from Diffusion NMR Logs, paper SS, presented at the 37$^{th}$ Annual Logging Symposium, SPWLA, New Orleans, La.

McKeon, D., Minh, C. C., Freedman, R., Harris, R., Willis, D., Davies, D., Gubelin, G., Oldigs, R., and Hurliman, M., 1999, An Improved NMR Tool Design for Faster Logging, paper CC, presented at the 40$^{th}$ Annual Logging Symposium, SPWLA, Oslo, Norway.

Prammer, M. G., Drack, E. D., Bouton, J. C., Coates, G. R., Chandler, R. N., and Miller, M. N., 1996, Measurements of Clay-Bound Water and Total Porosity by Magnetic Resonance Logging, SPE-36522, presented at the 1996 SPE Annual Technical Conference and Exhibition held in Denver, Colo.

Prammer, M. G., Drack, E. D., Bouton, J. C., Chandler, R. N., and Miller, M. N., 1998, A New Multiband Generation of NMR Logging Tools, SPE-4901 1, presented at the 1998 SPE Annual Technical Conference and Exhibition held in New Orleans, La.

Sigal, R. F., Miller, D. L., Galford, J. E., Cherry, R., and Day, P. I., 2000, A Method for Enhancing the Vertical Resolution of NMR Logs, SPE-63215, presented at the 2000 SPE Annual Technical Conference and Exhibition held in Dallas, Tex.

SUMMARY OF THE INVENTION

Accordingly, it is an object of the present invention to overcome deficiencies associated with the prior art and in particular to provide a method and system for improving the resolution of borehole NMR logging measurements and for suppressing artifacts in NMR data obtained from logging measurements.

In accordance with the present invention, a system and methods are proposed for improving the vertical resolution of NMR logs based on data acquisition methods and signal processing techniques that need not apply Phase Alternated Pair Stacking (PAPS). The method is based on reducing the level of coherent non-formation signals, by providing estimates of these signals and removing the estimates from the underlying NMR pulse echo trains. Once the estimated non-formation signal components have been removed, standard NMR processing methods are applied to derive petrophysical properties of the formation being investigated. In a preferred embodiment the NOPAPS method of this invention is practiced along with a data acquisition sequence, which can be used to further increase the logging speed of the tool or vertical resolution of the measurements.

In particular, in one aspect, the invention is a method for determining properties of geologic formations using NMR techniques, comprising the steps of: providing a plurality of NMR pulse echo trains from a geologic formation, said plurality of NMR pulse echo trains not including phase alternated pairs; estimating non-formation signal contribution in the plurality of NMR pulse echo trains; removing the estimated non-formation signal contribution from at least some of the plurality of NMR pulse echo trains; and determining properties of the geologic formation based at least in part on NMR pulse echo trains in which the estimated non-formation signal contribution had been removed. Preferably, the NMR pulse echo trains are Carr-Purcell-Meiboom-Gill (CMPG) spin echo trains, which can be stacked to reduce the contribution of random noise. In a preferred embodiment, the step of estimating non-formation signal contribution comprises the steps of: (i) rotating an input signal y(t) by the angle $-\theta s$, where $\theta s$ is the formation signal angle to obtain a rotated signal $y_R(t)$; (ii) separating the real and imaginary components of the rotated signal; and (iii) computing an estimate of the non-formation signal contribution based on at least one of the separated real and imaginary components of the rotated signal.

In another aspect, the invention is a method for increasing the resolution of NMR log data obtained using a multi-frequency NMR tool having N (N$\geq$2) operating frequencies, comprising: (a) providing NMR pulse echo trains having components corresponding to at least two operating frequencies of the tool, said plurality of NMR pulse echo trains not including phase alternated pairs; (b) processing the provided NMR pulse echo trains to remove coherent non-formation signal components; and (c) determining properties of the geologic formation based at least in part on NMR pulse echo trains in which the estimated non-formation signal contribution had been removed.

BRIEF DESCRIPTION OF THE DRAWINGS

The advantages of the present invention will become apparent from the following detailed description and the accompanying drawings, in which.

DETAILED DESCRIPTION OF THE PREFERRED EMBODIMENTS

I. The System

Figure 1:
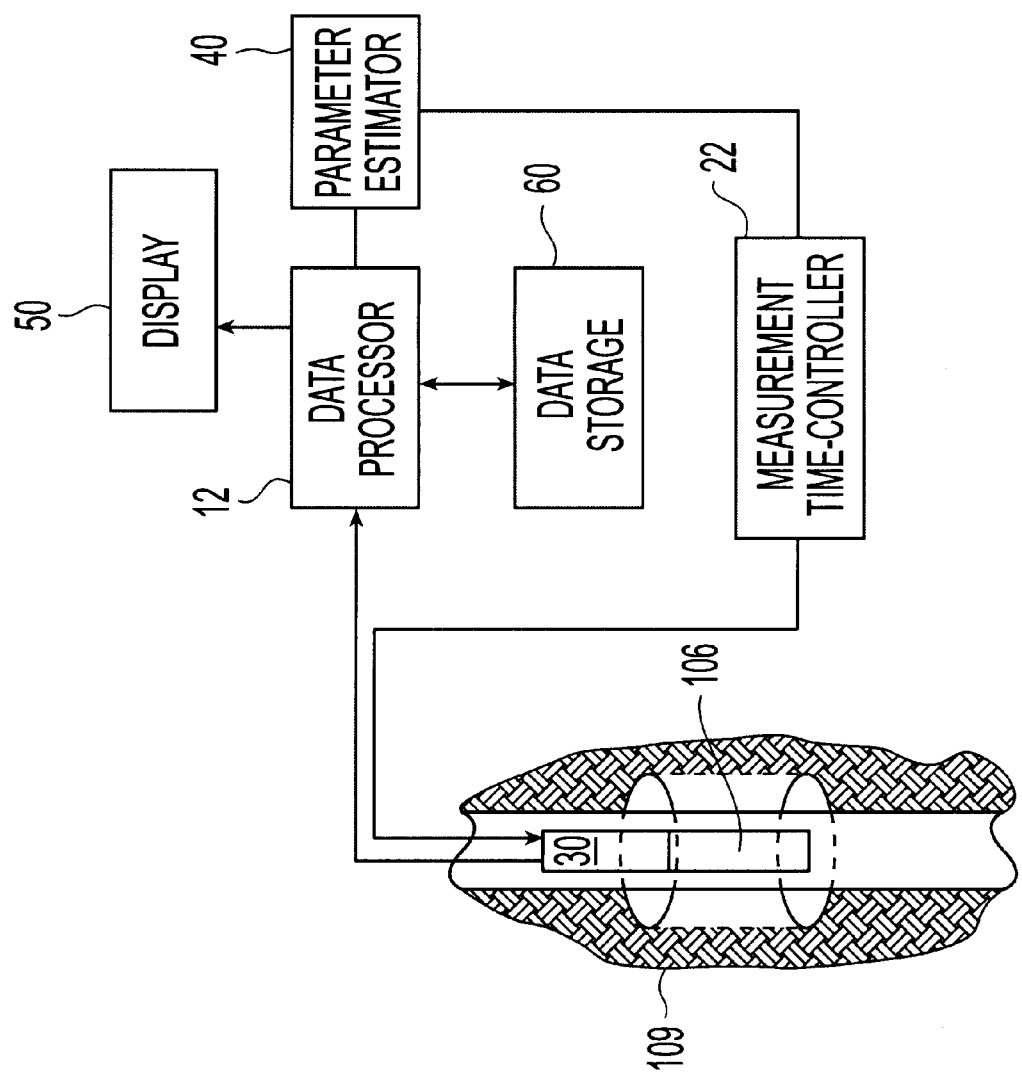
FIG. 1 is a block diagram of a system in accordance with a specific embodiment of the present invention.

FIG. 1 is a block diagram of a system in accordance with a specific embodiment of the present invention, which shows individual block components for controlling data collection, processing of the collected data and displaying the measurement results. In FIG. 1 a logging tool 106 comprises an NMR probe controller 30 and pulse echo detection electronics and is lowered in a borehole drilled in the formation 109. The output signal from the tool detection electronics is processed by data processor 12 to record NMR pulse echo data from the tool and analyze the relaxation characteristics of the materials surrounding the borehole. The output of the data processor 12 is fed to parameter estimator 40. Measurement cycle controller 22 provides an appropriate control signals to the probe. The processed data from the log measurements is stored in data storage 60. Data processor 12 is connected to display 50, which is capable of providing a graphical display of one or more measurement parameters, preferably superimposed on display data from data storage 60. The components of the system of the present invention shown in FIG. 1 can be implemented in hardware or software, or any combination thereof suitable for practical purposes.

In accordance with the present invention various NMR tools can be used in practical applications including, for example, the centralized MRIL® tool made by NUMAR Corporation, a Halliburton company, and the sidewall CMR tool made by Schlumberger. Details of the construction and operation of the MRIL-Prime® tool used in accordance with a preferred embodiment can be found in U.S. Pat. Nos. 4,710,713 4,717,876; 4,717,877; 4,717,878; 5,212,447; 5,280,243; 5,309,098; 5,412,320; 5,517,115, 5,557,200 and 5,696,448. Further details are provided in Prammer, et al., "A New Multiband Generation of NMR Logging Tools," SPE-49011, presented at the 1998 SPE Annual Technical Conference and Exhibition held in New Orleans, La. The content of the above references is hereby expressly incorporated by reference. It will be appreciated that while the MRIL® tool is used in a preferred embodiment, any other tool notably the CMR and CMR-Plus tools by Schlumberger, or other available tools, such as those by Baker-Atlas and Computalog, as well as logging-while-drilling (LWD) tools, appropriately programmed, can also be used in alternative embodiments.

II. Signal Processing Methods

In accordance with one aspect of the present invention, a novel approach is proposed for reducing the level of coherent non-formation signals, which may include both ringing and instrumentation biases. For simplicity, in the following description the term "bias" is used to refer to such coherent non-formation signals. In accordance with the invention, bias signals are estimated and removed from the underlying NMR pulse echo trains. Once the estimated bias component is removed from the acquisition sequence(s), in accordance with the invention, standard NMR processing methods are applied to derive petrophysical properties of the formation being investigated.

In particular, in accordance with the present invention a novel method is proposed in which no Phase Alternated Pair Stacking (PAPS), typical of the prior art NMR measurements, is applied in the pre-processing phase. Accordingly, the method is referred to next as "NOPAPS". Pre-processing can be defined as the series of processes applied to raw NMR signal to improve its signal-to-noise ratio (SNR) prior to inversion. Inversion is the transformation process where the time domain signal is inverted into a relaxation time distribution. The NOPAPS method in accordance with the present invention enables improved vertical resolution and/or increased logging speed, and differs from existing methods in that it does not require the existence of phase alternated pairs.

Figure 2:
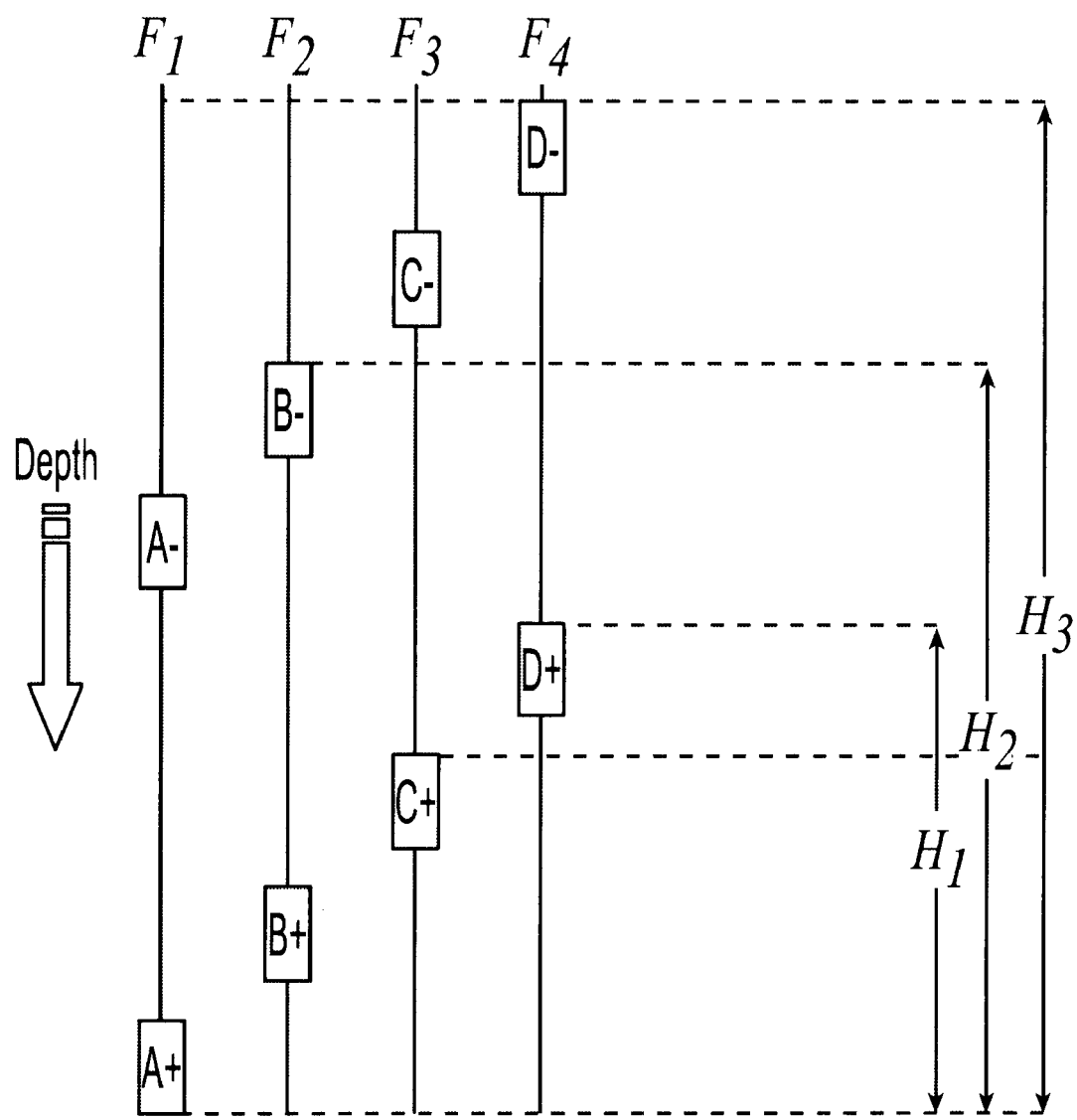
FIG. 2 illustrates a data acquisition protocol for a 4-frequency tool comparing the vertical resolution associated with the PAPS method of the prior art with the resolution of the NOPAPS method in accordance with the present invention.

FIG. 2 shows the timing diagram of a hypothetical activation, running on 4 frequencies. Assume that the noise level is such that stacking 4 CPMGs results in sufficient SNR for robust inversion. In the prior art, during acquisition the tool first acquires the plus phases over 4 frequencies (A+ to D+), then repeats the same pattern with the alternated phases (A− to D−). Given the stacking level of 4, PAPS based processing requires the stacking of sequences A+, B+, A− and B−, associated with the formation height $H_2$. Actually, the accepted practice is to stack all 8 sequences (A+ to D+, A− to D−) for efficiency, resulting in the formation height $H_3$.

For vertical resolution purposes, it would clearly have been better to stack the four adjacent CPMGs A+ to D+. The formation height associated with this approach, $H_1$, is superior to its PAPS based counterparts since $$H_1 < H_2 < H_3.$$

Stacking CPMGs A+ to D+, without their phase-alternated pairs requires a new process to remove the bias from the data. The NOPAPS method of this invention addresses this need.

In accordance with a preferred embodiment of the present invention, three steps are implemented, starting with the raw NMR signal in complex domain, to decouple the unwanted bias from the formation signal.

First, note that the raw NMR CPMG signal y(t) has three components: (1) the formation signal s(t), (2) the bias B, and (3) random noise components $n_x(t)$ and $n_y(t)$, and therefore can be expressed as:

$$y(t) = s(t)e^{j\theta s} + Be^{j\theta b} + n_x(t) + jn_y(t)$$

where j=sqrt(−1). In the above equation, $n_x(t)$ and $n_y(t)$ are zero-mean Gaussian and uncorrelated. The formation signal angle and the bias angle are denoted by θs and θb, respectively. Also, the NMR signal is actually a discrete function sampled at interecho time $T_e$, even though it is treated as a continuous function of time here for ease of notation.

The first step in accordance with the preferred embodiment is to rotate the complex signal by the angle −θs. In a preferred embodiment, the formation signal angle θs is estimated using the following simple non-linear minimization problem: minimize the error vector ε(t), where $$\epsilon(t) = Im\{y(t)e^{-jx_1}\} - x_2 e^{-t/T_L}$$

The vector of unknowns in the above expression has two components, i.e., $x = \{x_1, x_2\}$, where $x_1$ is the desired formation signal angle θs. In the above expression, the time constant $T_L$ is selected to a very large value, typically in the order of several seconds, whereas the independent time variable t is expressed in milliseconds. It will be appreciated that in a simplification of the this expression the exponential term $\exp(-t/T_L)$ can be replaced by a constant c=1. The second unknown $x_2$ can be retained for further processing. In a preferred embodiment the solution of the above problem can be found using the MATLAB® non-linear optimization software.

In an alternative embodiment, the determination of the angle θs can be done in a straightforward manner, if at least a portion of the NMR data is acquired using phase alternated pairs. In such case, it can be shown that the angle can be computed as:

$$\theta_s = \tan^{-1} \frac{\int_{2Te}^{kTe} \text{Im}\{y_{PAP}(t)\} dt}{\int_{2Te}^{kTe} \text{Re}\{y_{PAP}(t)\} dt}$$

where $T_e$ is the interecho time. It will be appreciated that because the variation in the angle θs is negligible over large depth intervals, using phase alternated pairs for the estimation of θs is different from and independent of the use of phase alternated pairs in the removal of the bias from the echo trains.

Once the angle θs is estimated, the resultant rotated signal $y_R(t)$ used in accordance with this invention is given by:

$$y_R(t) = y(t)e^{-j\theta_s} = s(t) + Be^{j(\theta_b - \theta_s)}$$

The random noise components $n_x(y)$ and $n_y(t)$ are omitted for the sake of simplicity in the above and all further expressions. The rotated signal $y_R(t)$ can be separated into its real and imaginary parts, resulting in the following expressions:

$$Re\{y_R(t)\} = s(t) + B\cos(\theta_b - \theta_s)$$

$$Im\{y_R(t)\} = B\sin(\theta_b - \theta_s)$$

It will be appreciated that in the above expressions, the real part of the rotated signal contains the formation signal and a projection of the bias, whereas the imaginary part of the rotated signal contains only bias information.

The next step in the preferred embodiment is to compute the following quantities:

$$p_x = \frac{1}{t_f - t_0} \int_{t_0}^{t_f} Re\{y_R(t)\} dt$$

$$p_y = \frac{1}{t_f - t_0} \int_{t_0}^{t_f} Im\{y_R(t)\} dt$$

Once again, continuous functions and integrals have been used for sake of simplicity. Note that the real and imaginary parts of $y_R(t)$ actually contain random noise components, not shown here for the sake of simplicity. The contributions to either $p_x$ or $p_y$, from the random noise components, is minimal due to the integration process applied to a zero-mean Gaussian signal. The time limits $t_0$ and $t_f$ are defined as follows:

$$0 < t_0 < N_e T_e = t_f$$

where $N_e$ is the number of echoes, $T_e$ is the interecho time, and $t_f$ is the upper limit of integration. The lower time limit $t_0$ is chosen such that s(t) is negligible for $t > t_0$. This criteria can always be met by appropriately selecting among the set of three acquisition parameters $\{T_e, N_e, T_w\}$, where $T_w$ is the wait time.

In an alternative embodiment of the invention, $p_y$ in the above expressions can be replaced by $P_y$, which is defined as follows:

$$P_y = \frac{1}{t_f} \int_0^{t_f} Im\{y_R(t)\} dt$$

It will be appreciated that $P_y$ is less sensitive to noise than $p_y$ because of the larger integration interval. $P_y$ and $p_y$ will be used interchangeably in the following discussion.

The last step of the method in a preferred embodiment is the extraction of the formation signal s(t) from the rotated signal $y_R(t)$. This step is implemented by one of the two expressions given below, depending on the value of $p_y$. In particular, If $p_y < p_{min}$, then $$s(t) = Re\{y_R(t)\} - p_x$$

where $p_{min}$ is a threshold that depends on the noise level and the integration interval. A typical value for $p_{min}$ is in the range of about 0.05 to 0.5 pu (porosity units). It will be appreciated that other values can be used in different embodiments.

If $p_y > p_{min}$, then the formation signal is computed as follows:

$$s(t) = Re\{y_R(t)\} - B\cos(\theta_b - \theta_s).$$

The quantities B and $\theta_b - \theta_s$ in the above expression are computed as follows:

$$(\theta_b - \theta_s) = \tan^{-1}\left(\frac{p_y}{p_x}\right)$$

$$B = \frac{p_y}{\sin(\theta_b - \theta_s)}$$

The three-step approach used in the preferred embodiment provides a simple mechanism to avoid the use of PAPS, and thus improve the resolution of the measurement and/or the logging speed of the tool as illustrated in the following examples.

III. EXAMPLES
Comparison of PAPS vs NOPAPS

Figure 3:
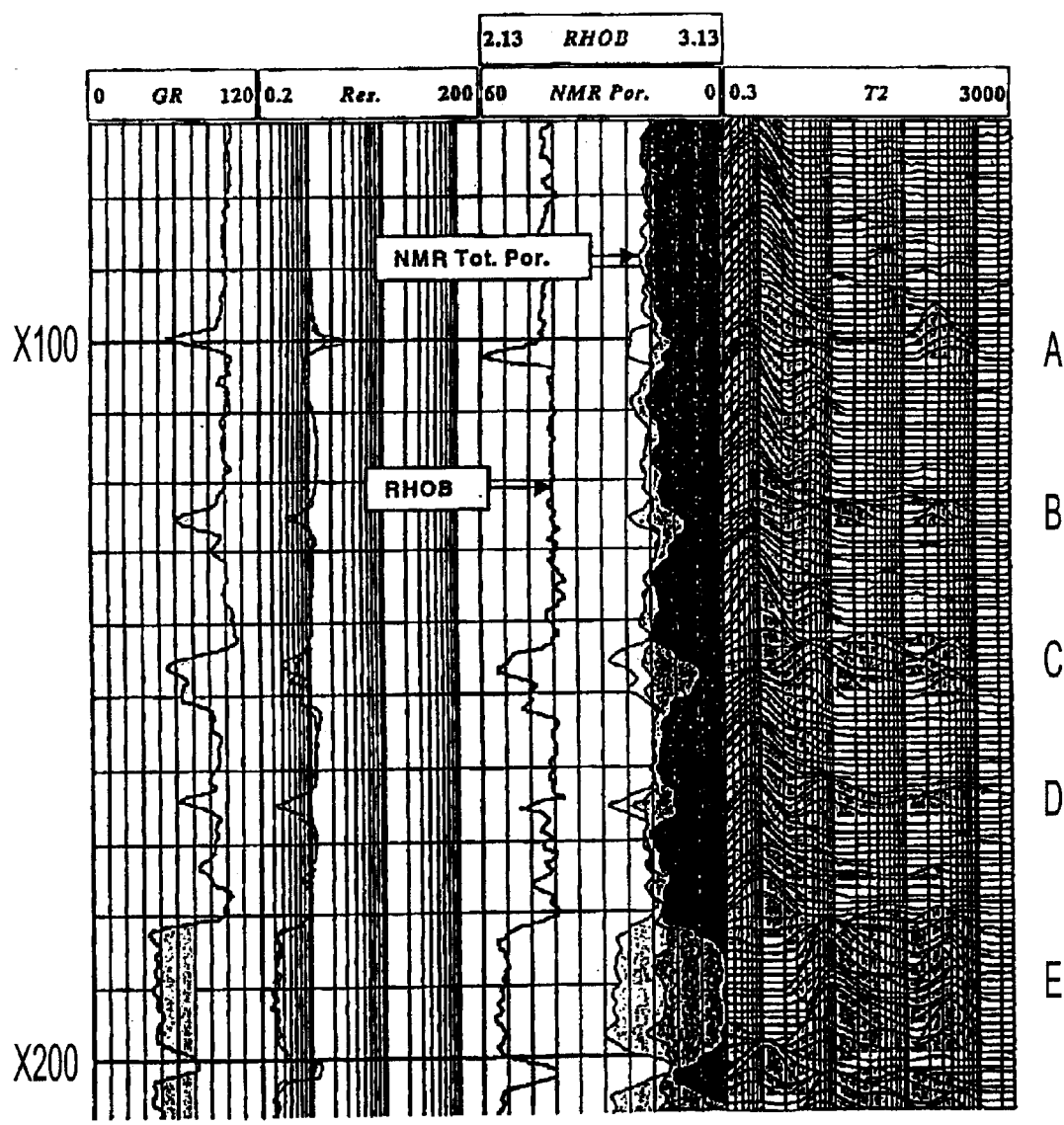
FIG. 3 illustrates results from the application of the NOPAPS method of this invention in a well drilled with OBM.
Figure 4:
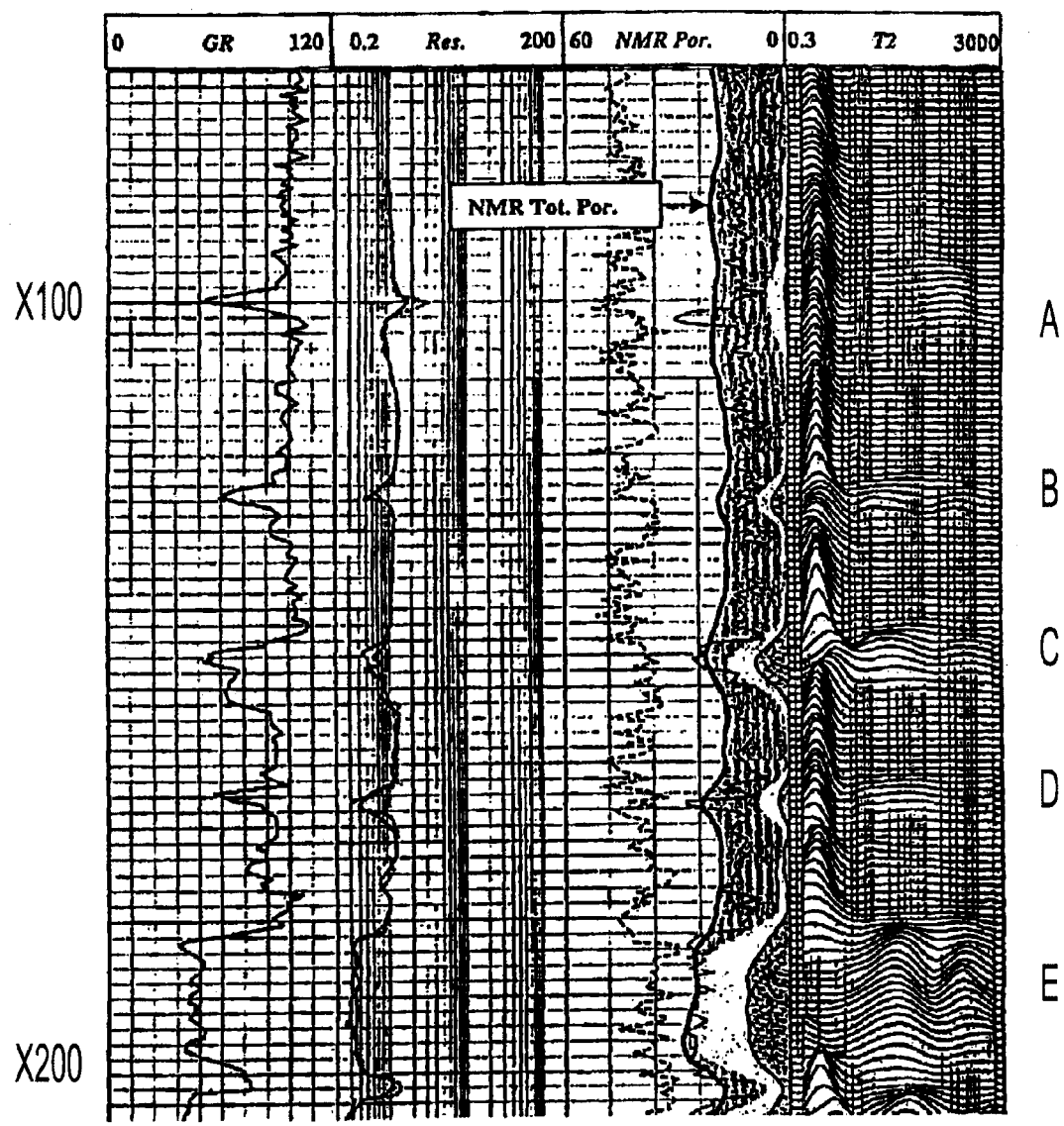
FIG. 4 illustrates PAPS results from the well drilled with OBM as illustrated in FIG. 3.

FIG. 3 illustrates standard open-hole and MRIL-Prime log results from a well drilled with oil-based mud (OBM). Gamma Ray is shown in Track 1, resistivity curves in Track 2, bulk density and NMR total porosity in Track 3, $T_2$ distributions in Track 4. NMR total porosity is divided into its free fluid, bound and microporosity components. Note the unusual scale used for the bulk density curve in Track 3, which was used in the illustration in order to allow better visual comparison with the NMR log. Vendor results for the same interval, processed using PAPS, are shown in FIG. 4. (Note that although NMR total porosity is divided into its free fluid, bound and microporosity components, the components are not displayed in the same order as in FIG. 3).

Several zones stand out in FIG. 3, when compared to FIG. 4. The vertical resolution of the NMR logging, obtained from the simultaneous conversion of fully and partially recovered data with different acquisition parameters and SNR, is remarkably similar to those of the other open hole logs.

The first feature to consider is a thin bed, 2 to 3 feet thick, at X100 (marked A on the right of the log). Note that the NMR log shows a blocky character, instead of the sharp feature seen in other logs. The bulky nature of the NMR log is due to tool sticking. In any case, this thin pay sand can clearly be seen in FIG. 3, but not in the case of PAPS processing illustrated in FIG. 4. For example, the total porosity log hardly changes in zone A in FIG. 4. If not for the presence of a free fluid show, the zone looks very similar to the shales above and below it.

Zone B centered at X125 is a thin-wet sand that shows up very clearly in the GR, resistivity and NOPAPS NMR logs in FIG. 3. Note the absence of response in the bulk density log, which is a mere bump in FIG. 4.

Zone C around X150 shows two thin beds: a relatively clean sand on top of an equally thin, but shalier sand. Note the strong correlation of the features among the open hole and NMR logs shown in FIG. 3. By contrast, a very different picture appears in FIG. 4. In particular, the PAPS processing has turned two distinct thin beds with varying degrees of shaliness into a single symmetric large bed.

Zone D in FIG. 3 has a very sharp signature, whereas it is very smooth and rounded in FIG. 4. Zone E is a thick wet sand, starting at X180. Note the one-to-one correspondence among the peaks and troughs of the NMR and open hole logs in FIG. 3. Once again, all the local features are lost in the PAPS-processed version shown in FIG. 4.

Figure 5:
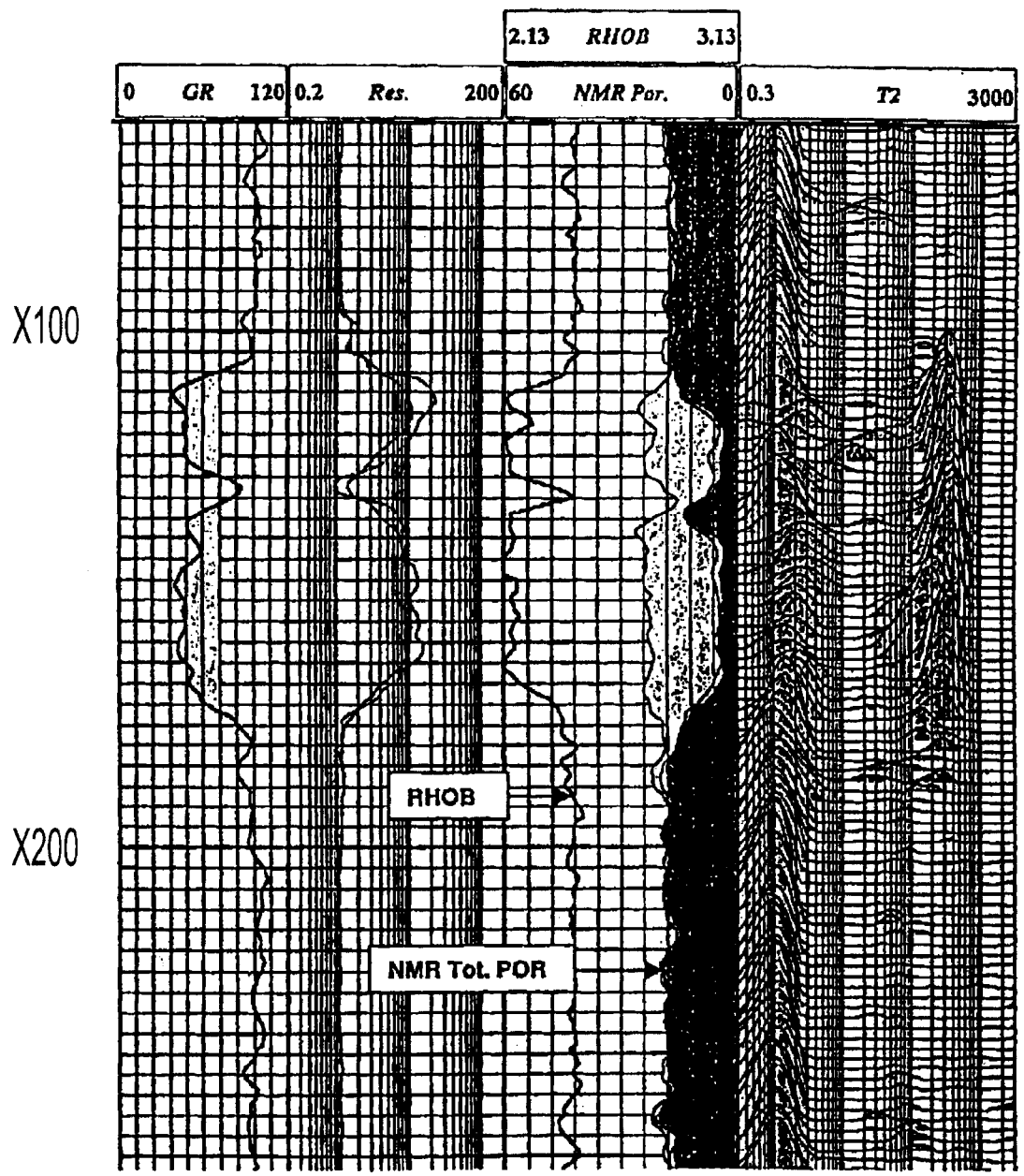
FIG. 5 shows another set of NOPAPS results from a well drilled with OBM, which illustrate the improvements, both in vertical resolution and $T_2$ distribution, in comparison to the prior art measurements illustrated in FIG. 6.
Figure 6:
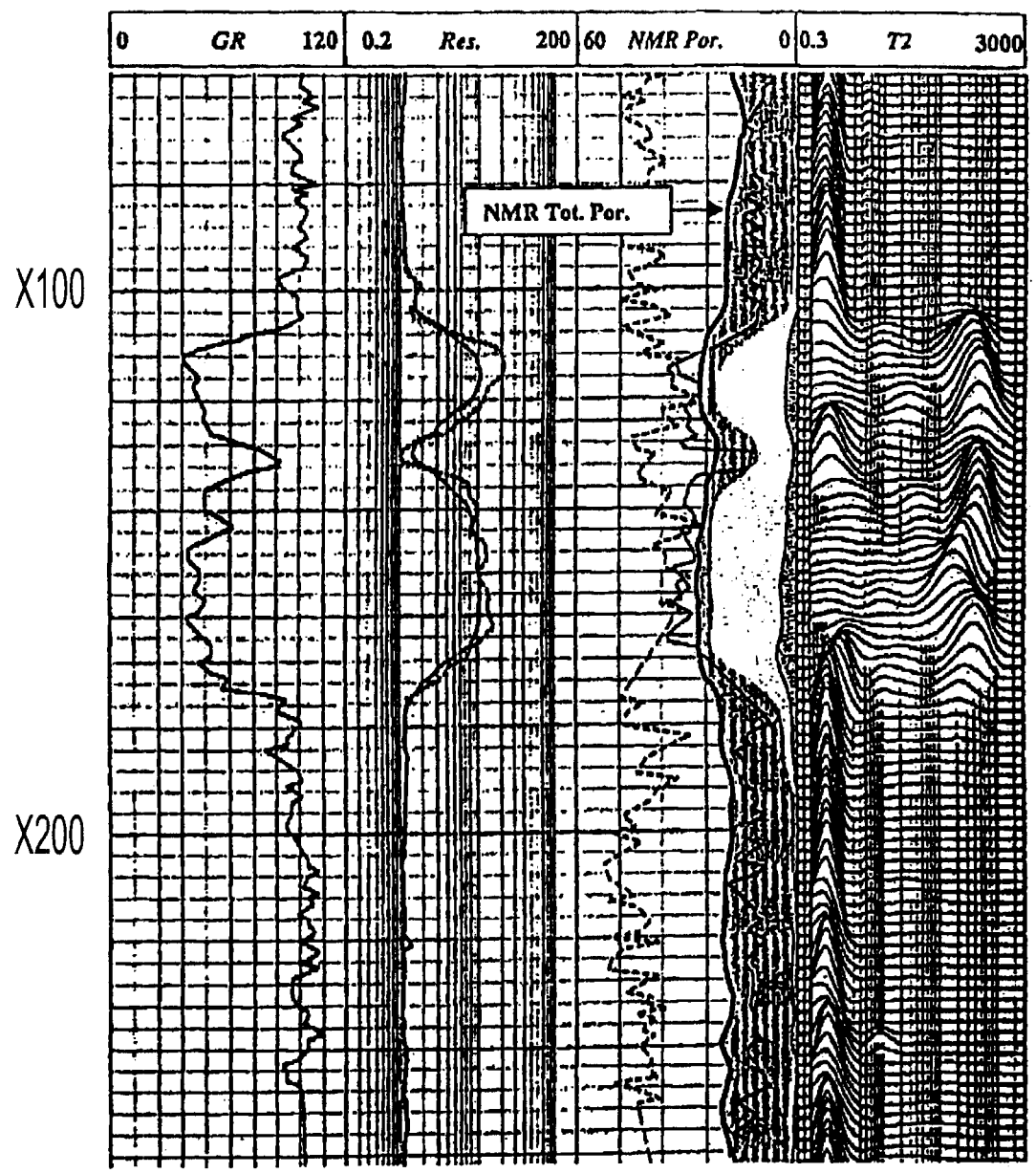
FIG. 6 illustrates PAPS results from the well drilled with OBM, as shown in FIG. 5.

FIG. 5 shows the NOPAPS processing results from a different zone in the same well. The logs are shown in the same order and scales as in FIG. 3. This zone starting at X100 contains pay, verified by the resistivity log, as well as the strongly bi-modal $T_2$ distribution in Track 4. Note the high resolution of the NMR log in FIG. 5 processed with the NOPAPS method, vs. its smoothly and slowly varying PAPS processed counterpart in FIG. 6.

Another difference that can be observed between the PAPS vs NOPAPS logs is the $T_2$ resolution. For example, consider the pay zone shown in FIGS. 5 and 6, verified by the high resistivity readings. In FIG. 5, NOPAPS processing has generated a very sharp bi-modal $T_2$ distribution, which is typically the case for a low viscosity hydrocarbon zone invaded with OPMF. Notice by contrast the smooth and broadened distributions in the PAPS-processed log shown in FIG. 6, a common feature for both the pay and wet zones. (It should be noted that in this case the NOPAPS processing is only partially responsible for the improved $T_2$ resolution: simultaneous inversion of the partially and fully recovered data may also have played a role in the overall results, as discussed in more detail next).

Based on the above, it is apparent that the NOPAPS method used in accordance with the present invention clearly improves the resolution of the log compared with the standard prior art PAPS method.

Data Acquisition Sequences

While the immediate effect of the NOPAPS method proposed in accordance with the present invention may appear as improved vertical resolution, it is expected that its biggest impact in the future will be in the ability to provide improved vertical resolution, as well as faster logging speeds than currently possible for a given resolution. The improved logging speed is obtained in accordance with another aspect of this invention using a novel data acquisition sequence, as described below.

Consider the data acquisition scheme shown in FIG. 2, where data points are acquired over four frequencies $F_1$, $F_2$, $F_3$, $F_4$, and four CPMGs are assumed to provide adequate SNR for inversion. The figure is drawn to scale in the depth direction to illustrate the timing of the measurements, where $N_e T_e$ is 1 second, and $T_w$ is approximately 4.5 seconds. As shown, the tool first sweeps the frequencies $F_1$ to $F_4$ to acquire the plus—phase sequences A+ to D+. It then repeats the pattern with the alternated phase to generate sequences A− to D−. Assume that each sequence contains 1000 echoes acquired at a $T_e$ of 1 milisecond. Using the NOPAPS method of the present invention, sequences A+ to D+are stacked to result in a vertical resolution illustrated as $H_1$. Further, $H_2$ in FIG. 2 is the vertical resolution for the stack of two PAPs, while $H_3$ is what would normally be achieved in practice by stacking all four PAPs.

In accordance with another aspect of the present invention data acquisition can be optimized by taking into account the observation that SNR requirements for accurately estimating longer decaying components are not as stringent as those for faster decaying components. For example, it is known in the art that results of similar quality may be obtained by simultaneously inverting two echo trains with 1000 echoes and two echo trains with 500 echoes, instead of four echo trains with 1000 echoes each. This observation is used in accordance with a preferred embodiment to generate an optimized data acquisition sequence, resulting in better vertical resolution and/or faster logging speed. The novel data acquisition sequence in accordance with the preferred embodiment is illustrated in FIG. 7.

Figure 7:
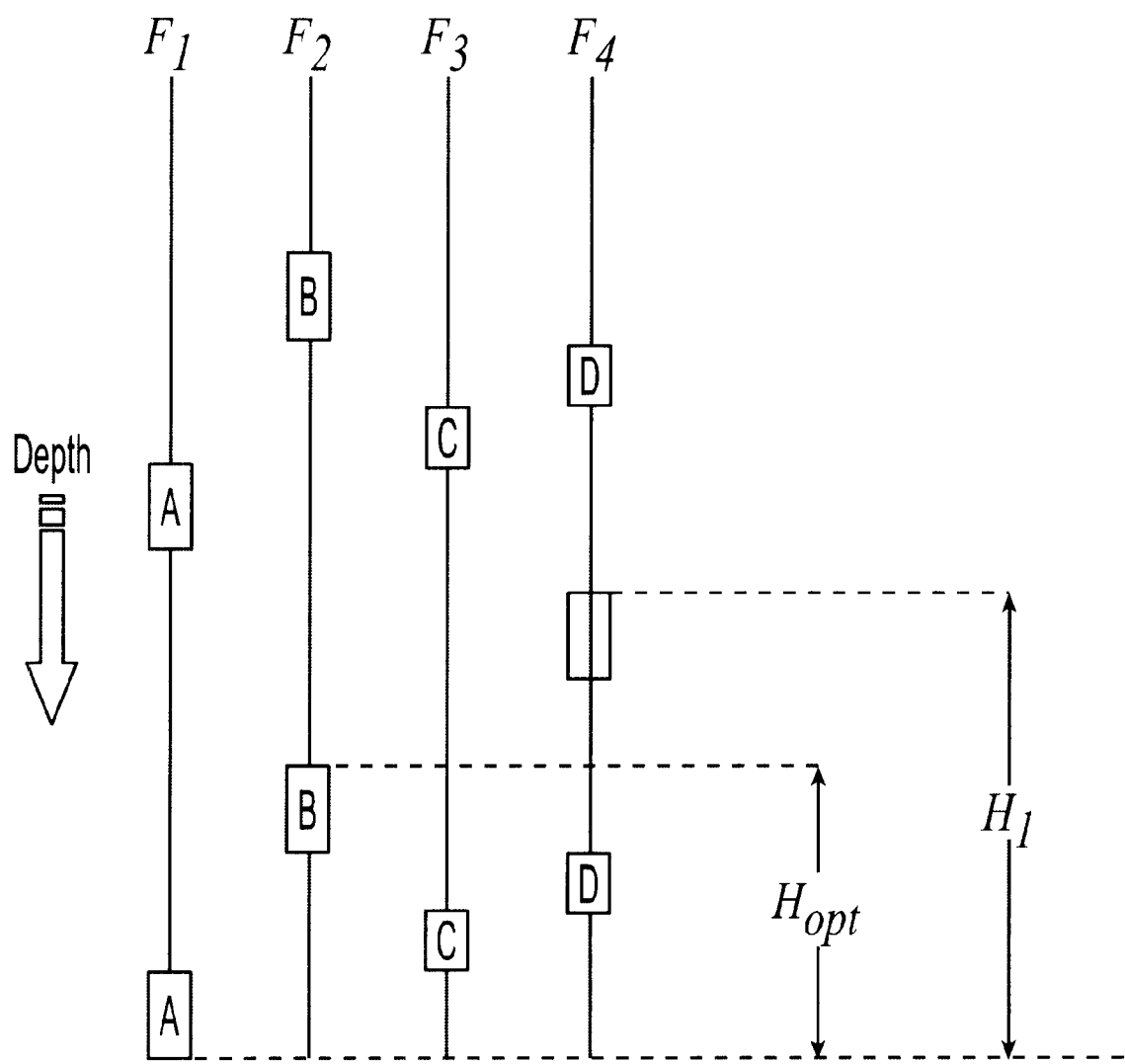
FIG. 7 illustrates an optimized data acquisition sequence applied in a preferred embodiment along with the NOPAPS method of this invention.

In particular, the data acquisition sequence in FIG. 7 is similar to FIG. 2, except that in a preferred embodiment sequences C and D take less time to acquire compared with sequences A and B. In a specific implementation, sequences C and D take half the time to acquire compared with A and B. Further, in accordance with the NOPAPS method of the present invention outlined above, there is no need for phase alternated pairs, and therefore only sequences A, B, C and D are used. As illustrated, the wait time between sequences has been kept the same as in FIG. 2. In the novel acquisition scheme according to this invention the tool sweeps frequencies out of order, first acquiring A in $F_1$, then C in $F_3$, D in $F_4$, and finally B in $F_2$. The pattern is then repeated. This new data acquisition scheme results in a better vertical resolution Hopt, which is compared in FIG. 7 to the resolution $H_1$, which can be obtained using the NOPAPS method, without the data acquisition optimization. For comparison purposes, the spatial location of the D+ sequence used in FIG. 2 is also shown. It will be appreciated that the optimized data acquisition of the preferred embodiment leads to a better vertical resolution $H_{opt}$, almost half of $H_1$.

Assuming next that $H_1$ is an acceptable vertical resolution, and taking into account the observation that $H_{opt}$ is approximately equal to $H_1/2$, it will be apparent that the logging speed can be increased by a factor of 2. Note that as a result of the application of the method of this invention the resulting log will exhibit both better vertical resolution and be obtained at faster logging speed.

Finally, it should be noted here that specific acquisition parameters, as well as the number of frequencies discussed above have been chosen as such for simplicity and illustration purposes only. In practical applications using, for example, the MRIL-Prime tool by Numar Corporation, a Halliburton Company, considerable improvement can be achieved because the tool operates on 9 frequencies, uses at most 600 milliseconds for $N_e T_e$, and about 12 seconds for $T_w$.

The NONPAPS method and associated data acquisition sequence discussed above is believed to present a significant contribution to the art of NMR logging with wide ranging applications involving virtually all NMR tools, and a broad range of practical applications, including logging-while-drilling (LWD), laboratory NMR equipment or medical imaging applications.

While the invention has been described with reference to the preferred embodiments, it will be appreciated by those of ordinary skill in the art that modifications can be made to the structure and form of the invention without departing from its spirit and scope which is defined in the following claims.

What is claimed is:

1. A method for determining properties of geologic formations using nuclear magnetic resonance (NMR) techniques, comprising the steps of:
   (a) providing one or more NMR pulse echo trains from a geologic formation, said NMR pulse echo trains not including phase alternated pairs;
   (b) estimating non-formation signal contribution in the one or more NMR pulse echo trains;

(c) removing the estimated non-formation signal contribution from at least some of the one or more NMR pulse echo trains; and (d) determining properties of the geologic formation based at least in part on NMR pulse echo trains in which the estimated non-formation signal contribution had been removed.

2. The method of claim 1 in which the NMR pulse echo trains are Carr-Purcell-Meiboom-Gill (CMPG) spin echo trains.

3. The method of claim 2 wherein non-formation signal contribution is estimated from one or more of the CPMG spin echo trains.

4. The method of claim 2 further comprising the step of stacking CPMG spin echo trains from which non-formation signal contributions have been removed to achieve a predetermined signal to noise ratio (SNR).

5. The method of claim 1, wherein the estimated non-formation signal contribution is subtracted on a component-by-component basis from at least one NMR pulse echo train to obtain a corrected NMR pulse echo train.

6. The method of claim 1, wherein the step of providing one or more NMR pulse echo trains is performed off-line.

7. The method of claim 1, wherein the step of estimating non-formation signal contribution comprises the steps of:

(i) rotating an input signal y(t) by the angle $-\theta_s$, where $\theta_s$ is the formation signal angle to obtain a rotated signal $y_R(t)$;

(ii) separating the real and imaginary components of the rotated signal; and (iii) computing an estimate of the non-formation signal contribution based on at least one of the separated real and imaginary components of the rotated signal.

8. The method of claim 7, wherein the formation signal angle $\theta_s$ is estimated using non-linear minimization techniques.

9. The method of claim 7, wherein the formation signal angle $\theta_s$ is estimated using phase alternated pairs of NMR pulse echo trains from the geologic formation.

10. The method of claim 7, wherein the separated real and imaginary components of the rotated signal are processed to compute the following quantities:

$$p_x = \frac{1}{t_f - t_0} \int_{t_0}^{t_f} \mathrm{Re}\{y_R(t)\}\, dt$$

$$p_y = \frac{1}{t_f - t_0} \int_{t_0}^{t_f} \mathrm{Im}\{y_R(t)\}\, dt$$

where $t_0$ and $t_f$ are defined as follows: $0 < t_0 < N_e T_e = t_f$, $N_e$ is the number of echoes, $T_e$ is the interecho time, and $t_0$ is chosen such that the formation signal s(t) is negligible for $t > t_0$.

11. The method of claim 10, wherein the step of removing the estimated non-formation signal contribution comprises:

If $p_y < p_{min}$, then $$s(t) = \mathrm{Re}\{y_R(t)\} - p_x$$

where $p_{min}$ is a threshold that depends on the noise level and the integration interval, and if $p_y > p_{min}$, then $$s(t) = \mathrm{Re}\{y_R(t)\} - B \cos(\theta_b - \theta_s)$$

where $$(\theta_b - \theta_s) = \tan^{-1}\left(\frac{p_y}{p_x}\right) \text{ and } B = \frac{p_y}{\sin(\theta_b - \theta_s)}.$$

12. The method of claim 1, wherein steps (a), (b), (c) are performed substantially in real time.

13. The method of claim 1, wherein at least steps (a), (b), (c) are performed in a logging-while-drilling (LWD) environment.

14. A method for increasing the resolution of NMR log data obtained using a multi-frequency NMR tool having N ($N \geq 2$) operating frequencies, comprising:

(a) providing a plurality of NMR pulse echo trains having components corresponding to at least two operating frequencies of the tool, said NMR pulse echo trains not including phase alternated pairs;

(b) processing at least one of the provided NMR pulse echo trains to remove coherent non-formation signal components; and (c) determining properties of the geologic formation based at least in part on NMR pulse echo trains in which the estimated non-formation signal contribution had been removed.

15. The method of claim 14 further comprising the step of stacking signal components corresponding to different operating frequencies to remove random noise signals.

16. The method of claim 14 in which the NMR pulse echo trains are Carr-Purcell-Meiboom-Gill (CMPG) spin echo trains.

17. The method of claim 16, wherein CPMG spin echo trains corresponding to at least two different operating frequencies have different number of spin echos.

18. The method of claim 17, wherein spin echo trains having fewer spin echos are used to estimate fast relaxation formation signals.

19. The method of claim 16, wherein CPMG spin echo trains corresponding to at least two different operating frequencies differ in one or more of the following parameters: interecho spacing $T_e$, wait time $T_w$, recovery time $T_R$, and signal to noise ratio (SNR).

20. A system for determining properties of geologic formations using nuclear magnetic resonance (NMR) techniques, comprising the steps of:

means for providing one or more NMR pulse echo trains from a geologic formation, said one or more NMR pulse echo trains not including phase alternated pairs;

means for estimating non-formation signal contribution in the NMR pulse echo trains;

means for removing the estimated non-formation signal contribution from at least some of the NMR pulse echo trains; and means for determining properties of the geologic formation based at least in part on NMR pulse echo trains in which the estimated non-formation signal contribution had been removed.

21. A system for increasing the resolution of NMR log data obtained using a multi-frequency NMR tool having N ($N \geq 2$) operating frequencies, comprising:

(a) means for providing a plurality of NMR pulse echo trains having components corresponding to at least two operating frequencies of the tool, said NMR pulse echo trains not including phase alternated pairs;

(b) means for processing at least one of the provided NMR pulse echo trains to remove coherent non-formation signal components; and (c) means for determining properties of the geologic formation based at least in part on NMR pulse echo trains in which the estimated non-formation signal contribution had been removed.

22. The system of claim 21 further comprising means for stacking signal components corresponding to different operating frequencies to remove random noise signals.

23. The system of claim 21 in which the NMR pulse echo trains are Carr-Purcell-Meiboom-Gill (CMPG) spin echo trains.

24. The system of claim 23, wherein spin echo trains having fewer spin echos are used to estimate fast relaxation formation signals.

25. The method of claim 23, wherein CPMG spin echo trains corresponding to at least two different operating frequencies differ in one or more of the following parameters: interecho spacing $T_e$, wait time $T_w$, recovery time $T_R$, and signal to noise ratio (SNR).

* * * * *